United States Patent
Park et al.

(10) Patent No.: US 9,092,051 B2
(45) Date of Patent: Jul. 28, 2015

(54) METHOD FOR OPERATING USER FUNCTIONS BASED ON EYE TRACKING AND MOBILE DEVICE ADAPTED THERETO

(71) Applicant: Samsung Electronics Co., Ltd., Gyeonggi-do (KR)

(72) Inventors: Kyungdae Park, Seoul (KR); Jiyoung Kang, Gyeonggi-do (KR); Sanghyuk Koh, Seoul (KR); Mijung Park, Gyeonggi-do (KR); Saegee Oh, Gyeonggi-do (KR); Chihoon Lee, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 105 days.

(21) Appl. No.: 13/681,719

(22) Filed: Nov. 20, 2012

(65) Prior Publication Data

US 2013/0135196 A1    May 30, 2013

(30) Foreign Application Priority Data

Nov. 29, 2011 (KR) .......................... 10-2011-0125911

(51) Int. Cl.
  *G06F 3/01* (2006.01)
  *A61B 3/113* (2006.01)
  *G06F 3/0481* (2013.01)
  *G06F 3/0483* (2013.01)

(52) U.S. Cl.
  CPC . *G06F 3/01* (2013.01); *A61B 3/113* (2013.01); *G06F 3/013* (2013.01); *G06F 3/0481* (2013.01); *G06F 3/0483* (2013.01)

(58) Field of Classification Search
  CPC ............. G06F 3/00; G06F 3/01; G06F 3/013; G06F 3/048; G06F 3/0481; G06F 3/0482; G06F 3/04842; G06F 3/0483; A61B 3/113; G06K 9/00597
  See application file for complete search history.

(56) References Cited

U.S. PATENT DOCUMENTS

| | | | |
|---|---|---|---|
| 5,850,211 A | | 12/1998 | Tognazzini |
| 6,665,805 B1* | | 12/2003 | Tsirkel et al. .................. 713/323 |
| 8,340,365 B2* | | 12/2012 | Thorn et al. ................... 382/118 |
| 8,436,804 B2* | | 5/2013 | Liu et al. ........................ 345/102 |
| 8,594,374 B1* | | 11/2013 | Bozarth ......................... 382/103 |
| 8,643,680 B2* | | 2/2014 | Baldwin et al. ................ 345/684 |
| 2003/0052903 A1* | | 3/2003 | Weast ............................ 345/690 |
| 2006/0192775 A1* | | 8/2006 | Nicholson et al. ............ 345/211 |
| 2006/0256083 A1* | | 11/2006 | Rosenberg ..................... 345/156 |
| 2007/0078552 A1* | | 4/2007 | Rosenberg ....................... 700/94 |
| 2007/0176898 A1* | | 8/2007 | Suh ................................ 345/158 |
| 2008/0111833 A1* | | 5/2008 | Thorn et al. ................... 345/690 |
| 2009/0082066 A1 | | 3/2009 | Katz |

(Continued)

FOREIGN PATENT DOCUMENTS

EP         0 816 980 A2    1/1998
EP         2 333 640 A1    6/2011
KR   10-2011-0017236 A    2/2011

*Primary Examiner* — Dwayne Bost
*Assistant Examiner* — Ivelisse Martinez Quiles
(74) *Attorney, Agent, or Firm* — Cha & Reiter, LLC

(57) ABSTRACT

An eye tracking based user function controlling method and a mobile device adapted thereto are provided. A camera unit of a mobile device is activated while a specific user function is executed. A gaze angle of a user's eye is acquired from an image obtained via the camera unit. An eye tracking function is executed in which execution state is controlled according to the gaze angle.

20 Claims, 7 Drawing Sheets

(56) References Cited

U.S. PATENT DOCUMENTS

| | | |
|---|---|---|
| 2009/0271734 A1 | 10/2009 | Hsu et al. |
| 2009/0273562 A1* | 11/2009 | Baliga et al. .................. 345/157 |
| 2010/0079508 A1* | 4/2010 | Hodge et al. .................. 345/697 |
| 2010/0125816 A1* | 5/2010 | Bezos .......................... 715/863 |
| 2011/0115883 A1 | 5/2011 | Kellerman et al. |
| 2012/0083312 A1* | 4/2012 | Kim ........................... 455/556.1 |
| 2012/0105490 A1* | 5/2012 | Pasquero et al. .............. 345/690 |
| 2012/0288139 A1* | 11/2012 | Singhar ........................ 382/103 |
| 2012/0293528 A1* | 11/2012 | Larsen ......................... 345/156 |
| 2013/0057573 A1* | 3/2013 | Chakravarthula et al. .... 345/619 |
| 2013/0114850 A1* | 5/2013 | Publicover et al. ........... 382/103 |

* cited by examiner

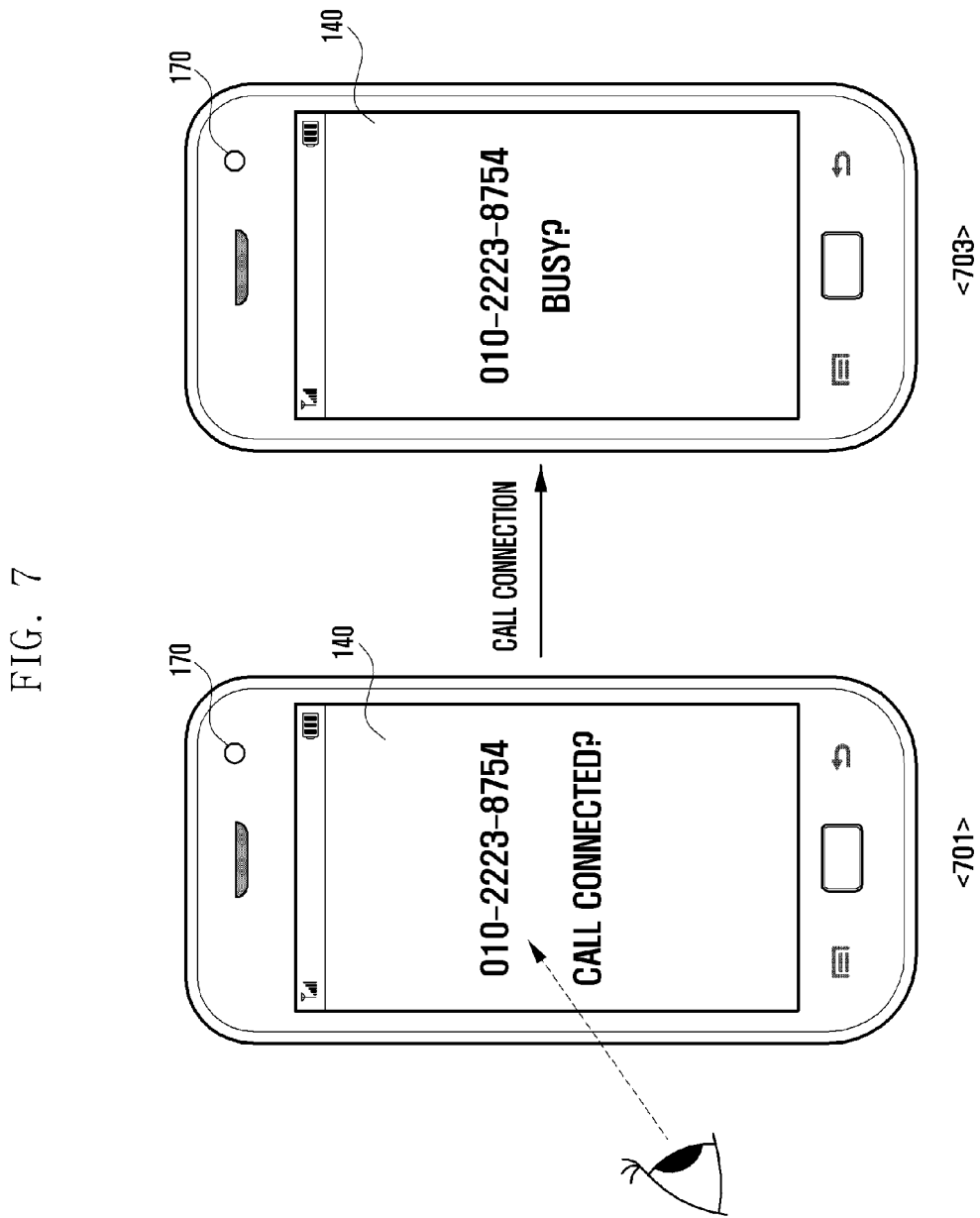

METHOD FOR OPERATING USER FUNCTIONS BASED ON EYE TRACKING AND MOBILE DEVICE ADAPTED THERETO

CLAIM OF PRIORITY

This application claims the benefit under 35 U.S.C. §119 (a) of a Korean patent application filed on Nov. 29, 2011 in the Korean Intellectual Property Office and assigned Serial No. 10-2011-0125911, the entire disclosure of which is hereby incorporated by reference.

BACKGROUND

1. Technical Field

This disclosure relates generally to controlling user functions and conserving power in electronic devices, and in particular, in mobile communication devices.

2. Description of the Related Art

Mobile devices such as smart phones and tablet PCs have become widely popular due to their portability and support of a wide variety of user functions. Recent designs provide integrated user functions, such as a camera function in conjunction with storing acquired photographs and videos, immediately searching for the acquired photographs or videos, etc. As newer models of mobile devices are equipped with relatively large displays, although they're still easily hand carried, a tradeoff in user controllability has arisen. For example, a notebook sized tablet can be held by one hand while the user touches the display with the same hand or the other hand; however, he/she may be unable to continue holding it stably due to the weight and size. This may cause a variety of problems, such as the user losing his/her grip of the mobile device, or causing a muscle injury.

To conserve battery power, conventional mobile devices change state from a normal state, in which the display has normal brightness, to a power save state in which the display is dimmed or shut off (the latter is referred to herein as a sleep state). The transition to the power save state is made after a predetermined elapsed time of not receiving any user input, such as a touch input command. This elapsed time is essentially a predicted time where the user is no longer actively viewing the display. To this end, a state control function is set under conditions set by default or by preference settings.

However, the set conditions may not always match a particular user's interaction with the mobile device. For example, the predetermined elapsed time that triggers the transition from normal mode to sleep mode is a fixed value, not adaptively varied according to the user's state or the environment. Therefore, the conventional mobile device may enter a power save or sleep mode at an undesirable time point, e.g. when the user still wants to use the device. In this case, the user must apply an additional operation to the mobile device, e.g., an awaking operation. The additional operation inconveniences mobile device users, and in particular, users of devices with larger displays which tend to be more actively utilized. Furthermore, if the elapsed time for transitioning to a power save mode is set too long, battery power is essentially wasted in the time period after the user stops viewing the display but prior to the elapsed time point.

SUMMARY

Disclosed herein is a method that can control efficiently and adaptively user functions of a mobile device, based on eye tracking, and a mobile device adapted to the method.

In accordance with an exemplary embodiment of the invention, a mobile device that controls user functions based on eye tracking is provided, including: a camera unit that acquires images of a subject; a controller configured to acquire a gaze angle of a user's eye from an image acquired via the camera unit, and to execute an eye tracking function in which an execution state of a user function is controlled according to the gaze angle; and a storage unit that stores data corresponding to the user function, and a program to track gaze angles of a user's eye.

Also provided is a method for operating user functions in a mobile device based on eye tracking. A camera unit of the mobile device is activated while a specific user function is executed. A gaze angle of a user's eye is acquired from an image obtained via the camera unit. An eye tracking function is executed in which execution state is controlled according to the gaze angle.

BRIEF DESCRIPTION OF THE DRAWINGS

The features and advantages of the invention will become more apparent from the following detailed description viewed in conjunction with the accompanying drawings, in which:

FIG. 7 illustrates screens to describe a method for making a call based on eye tracking, according to an embodiment of the invention.

DETAILED DESCRIPTION OF EXEMPLARY EMBODIMENTS

Figure 1:
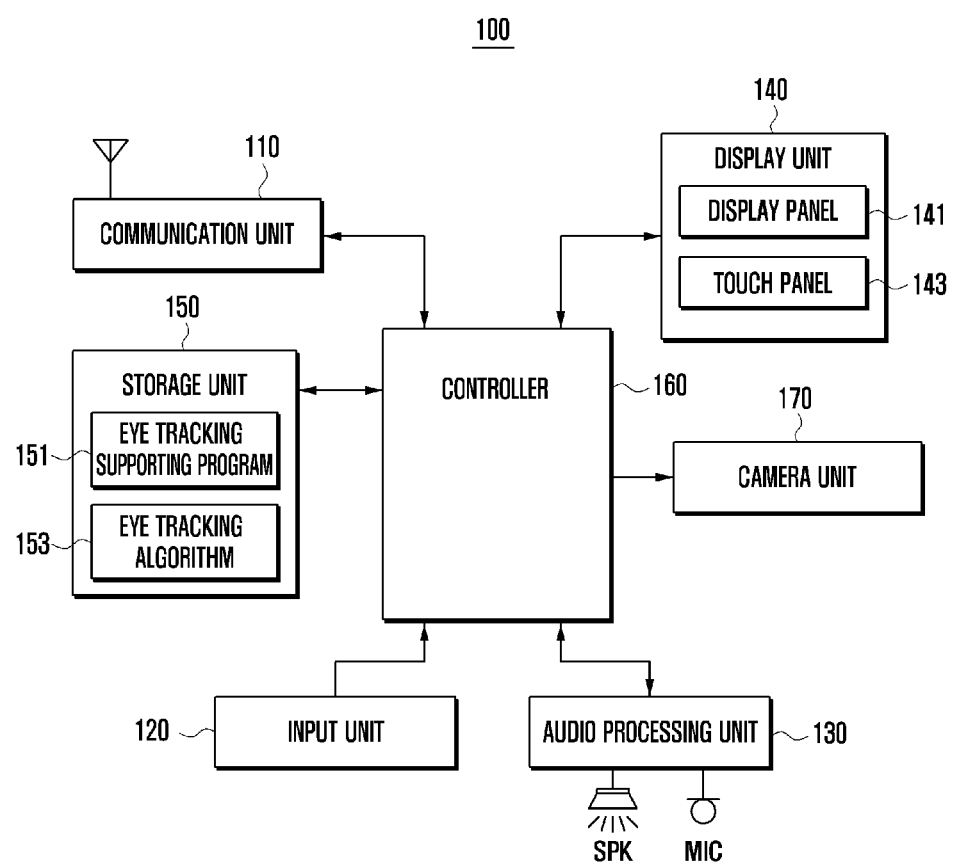
FIG. 1 illustrates a schematic block diagram of a mobile device with an eye tracking function, according to an embodiment of the invention.

Hereinafter, exemplary embodiments of the invention are described in detail with reference to the accompanying drawings. For the purposes of clarity and simplicity, detailed descriptions of well-known functions and structures incorporated herein may be omitted to avoid obscuring the subject matter of the invention. A detailed description of configurations that includes the same elements and performs the same functions will not be explained repeatedly in the description.

Although the drawings represent embodiments of the invention, the drawings are not necessarily to scale and certain features may be exaggerated or omitted in order to better illustrate and explain the invention. It should be understood that the invention is not limited to the drawing scale.

It is to be understood that the singular forms "a", "an" and "the" include plural referents unless the context clearly dictates otherwise. Thus, for example, reference to "a component surface" includes reference to one or more of such surfaces.

FIG. 1 illustrates a schematic block diagram of a mobile device 100 with an eye tracking function, according to an embodiment of the invention. A mobile device according to the invention can be any information communication device, multimedia device, etc., operated according to communication protocols corresponding to various types of communication systems. Examples of a mobile device include mobile communication terminals, Portable Multimedia Players (PMPs), digital broadcast players, Personal Digital Assistants (PDAs), audio players (e.g., MP3 players), mobile game players, smart phones, laptop computers, hand-held PC, etc.

Mobile device 100 includes a communication unit 110, an input unit 120, an audio processing unit 130, a display unit 140, a storage unit 150, a camera unit 170 and a controller 160.

When a specific user function is executed or a specific state is activated in the mobile device 100, the mobile device 100 automatically activates the camera unit 170 and controls it to acquire images at a certain angle. The mobile device 100 measures the motion of a user's eyes using the acquired images, via eye tracking, and identifies the direction of the user's gaze. If the direction of the user's gaze is a preset direction, the mobile device 100 generates a command corresponding thereto. After that, the mobile device 100 alters or maintains the current state or executes a function, according to the generated command. Since the mobile device 100 can be controlled according to the user's gaze, the user can manage operations easily, adaptively, and effectively on the mobile device 100.

The communication unit 110 supports communication of the mobile device 100, and is implemented with a module for supporting communication, in particular, mobile communication. The communication unit 110 establishes communication channels with a mobile communication system and transmits/receives signals thereto/therefrom. For example, the communication unit 110 establishes at least one of voice, video, and data service channels with a mobile communication system, and transmits/receives corresponding signals via the channels. (It is noted here, that if mobile device 100 is implemented without supporting a communication function, the communication unit 110 can be omitted.)

The communication unit 110 may also perform operations associated with the camera unit 170. For example, if the mobile device 100 receives, via the communication unit 110, a call connection request message or a message replying to the reception of a service message, from another mobile device, the controller 160 outputs information indicating the message has been received to the display unit 140 and/or the audio processing unit 130. During this process, the controller 160 may transfer the signal corresponding to the message reception event from the communication unit 110 to the camera unit 170. That is, when eye tracking mode is activated, if the communication unit 110 receives a message, the camera unit 170 is activated for a preset period of time and takes a video at a preset angle, which is used to support eye tracking. The controller 160 detects the user's eyes and the eye angles for eye tracking from the video acquired via the camera unit 170, and controls the communication unit 110 based on the detection. That is, an exemplary eye tracking mode can be established for facilitating acceptance of incoming calls. In this mode, when an incoming call is received, if the user gazes at the mobile device 100 display, a call connection request message is automatically transmitted, replying to the incoming call via the communication unit 110, thereby establishing the call connection therebetween. Thus if the mobile device 100 receives a call connection request message from the other mobile device, it can establish the call connection with the other mobile device automatically if the user gazes the mobile device 100, without requiring an additional operation. In another embodiment, an automatic call connection of the mobile device 100 with the other mobile device is implemented via face recognition (identification), in such a way that if the mobile device 100 identifies a predefined face, it performs the automatic call connecting process.

The input unit 120 generates signals required for the operations of the mobile device 100. The input unit 120 may be implemented with a keyboard, a keypad, key buttons, etc. according to the compatibility with the mobile device. If the display unit 140 is implemented with a touch screen, the touch screen performs at least part of the functions of the input unit 120 (although touch panel 143 is shown as part of display unit 140). In an embodiment of the invention, the input unit 120 generates input signals for supporting an eye tracking function according to a user's command, for example, signals for executing or releasing the eye tracking mode, signals for calling user functions associated with the eye tracking function, signals for associating an eye tracking function with a user function, etc. The input unit 120 transfers the generated input signals to the controller 160, and the controller 160 executes corresponding functions according to the input signals.

The audio processing unit 130 outputs audio signals that are set during the operations of the mobile device 100, generated when audio files stored in the storage unit 150 are played back, or received from the outside. The audio processing unit 130 also supports an audio signal collecting function. To this end, the audio processing unit 130 includes a speaker (SPK) and a microphone (MIC). In an embodiment of the invention, when a user function set with eye tracking is initially activated, the audio processing unit 130 outputs the corresponding audio signal indicating that the eye tracking function is being executed. If the mobile device 100 that can support an eye tracking function has not executed the eye tracking function, the audio processing unit 130 may output an audio signal informing the user that a corresponding eye tracking function may be set. Note that an audio signal is only output at the time the tracking function is initially set. This audio signal outputting function may be disabled according to the user's settings.

The time point that the audio processing unit 130 outputs an audio signal may be controlled via eye tracking. For example, the audio processing unit 130 may be controlled in such a way that it outputs an audio signal for a currently executed function only if the camera unit 170 acquires a user's gaze angle to the mobile device 100, corresponding to a preset angle; however it stops outputting the audio signal if the user gazes at the mobile device 100 at an angle other than the preset gaze angle. Herein, reference to a "gaze angle" signifies a gaze angle with a tolerance range, as will be understood by those skilled in the art. Thus, an angle other than a preset gaze angle means an angle outside the predetermined tolerance range of the preset gaze angle. In other words, "gaze angle" should be understood to mean "gaze angle range" when the application so dictates.

The display unit 140 provides a variety of screen interfaces required for the operations of the mobile device 100. For example, the display unit 140 supports an idle screen, menu screens, etc. In an embodiment of the invention, the display unit 140 provides a screen according to the execution of a user function associated with eye tracking, a setting screen for associating a user function with an eye tracking function, a screen for enabling or disabling an eye tracking function, etc.

The display unit 140 may be implemented with a touch screen. In this case, the touch screen includes a display panel 141 and a touch panel 143, where the touch panel 143 is installed at the front of the display panel 141 (hereinbelow referred to as just "the display" or "the screen" for brevity). The display panel 141 displays images, text, etc., corresponding to the variety of screens described above. The touch panel 143 includes a touch effective area and a non-touch effective area, defined according to the features of the screens displayed on the display panel 141, and transfers a signal corresponding to a touch event that occurs on the touch effective area to the controller 160. The touch panel 143 may be activated via eye tracking. For example, if the user views the mobile device 100 at a preset gaze angle, the touch panel 143 is activated and detects the presence of a touch event according to his/her touch action. On the other hand, if the user views the mobile device 100 at an angle other than the preset gaze angle, the touch panel 143 is disabled. The mobile device 100 may be implemented in such a way that it supports a temporary lock function or unlock function via eye tracking.

The storage unit 150 stores an operation system, application programs implementing algorithms, data, etc., required for the operation of the mobile device 100. In an embodiment of the invention, the storage unit 150 stores an eye tracking supporting program 151 for supporting eye tracking functions, and an eye tracking algorithm 153 for tracking a gaze angle of the user's eye in order to support the eye tracking supporting program 151.

In exemplary implementations, the eye tracking supporting program 151 includes a number of routines related to the operation of eye tracking functions as follows: a routine for activating the camera unit 170 if a user function associated with eye tracking is executed; a routine for acquiring images via the activated camera unit 170; a routine for recognizing the face and eyes from the acquired images; a routine for identifying the gaze angle of the eyes based on the recognition result; and a routine for controlling a currently executed user function according to the identified gaze angle. "User functions" as used herein refer to a variety of functions executed in the mobile device 100, via the components, e.g., the communication unit 110, display unit 140, audio processing unit 130, etc. Examples of user functions are a call function, a content file playback function, a file search function, a web access function, a function for outputting an idle screen, menu screens, etc., a broadcast receiving function, etc.

The eye tracking algorithm 153 analyzes images acquired by the camera unit 170 activated via the eye tracking supporting program 151. The eye tracking algorithm 153 can include both a face recognition algorithm and an iris recognition algorithm. Here, "face recognition" refers to a detection of the presence of any imaged face in the field of view of camera unit 170, not necessarily a particular person's face. That is, an identity detection is not required for the face recognition of the embodiments herein. Briefly, the eye tracking supporting program may operate as follows: when the camera unit 170 acquires an image, the program recognizes the outline of a face in the acquired image via the face recognition algorithm of the eye tracking algorithm 153. The eye portion is then extracted from the recognized face image, and then information is acquired regarding the gaze angle of the eyes from the eye portion. The program compares the acquired gaze angle with predefined information, and supports the state alteration of a currently executed user function, which will be described in detail later referring to the accompanying drawings.

The camera unit 170 is activated and acquires images, under the control of the controller 160. If the mobile device 100 is set in such a way that a user function associated with eye tracking is activated or an eye tracking function is activated by default, the camera unit 170 is activated and acquires images when the mobile device 100 is activated. The camera unit 170 transfers the acquired images to the controller 160, and the controller 160 analyzes them according to the eye tracking function. The acquired images refer to still images acquired periodically at regular intervals or a video acquired in real time. If the execution of a user function associated with an eye tracking function is terminated, the camera unit 170 may be automatically disabled (until activated by the user in a camera mode).

The controller 160 controls the flow of signals, the information collection, and the output operation, in order to support the eye tracking function associated with images acquired by the camera unit 170. To this end, the controller 160 supports an image collecting function and an information analyzing function, and controls user functions via these two functions.

Figure 2:
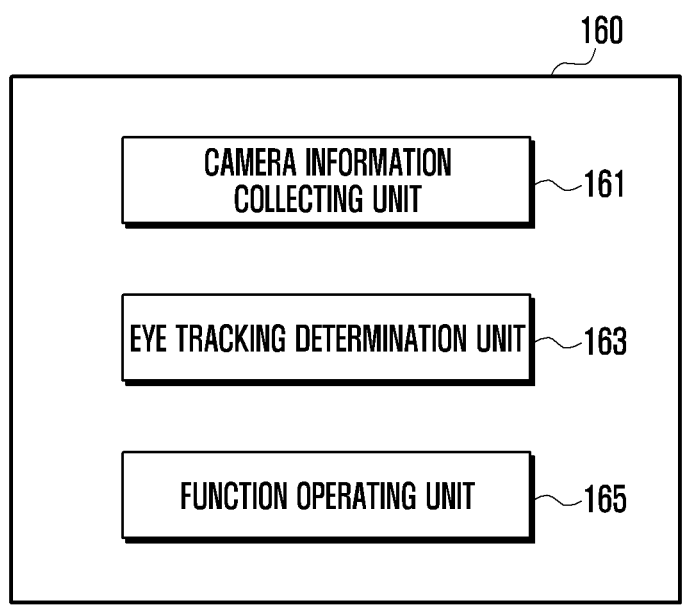
FIG. 2 illustrates an exemplary configuration of the controller shown in FIG. 1.

FIG. 2 illustrates a functional block diagram of an exemplary controller 160 shown in FIG. 1. Controller 160 includes a camera information collecting unit 161, an eye tracking determination unit 163, and a function operating unit 165.

The camera information collecting unit 161 determines, if a specific user function is activated, whether the user function is associated with an eye tracking function; if so, the controller activates the camera unit 170. The camera information collecting unit 161 sets the camera unit 170 according to preset values and controls it to acquire images. The camera information collecting unit 161 executes the face recognition process with respect to the user's face and allows the camera unit 170 to automatically focus on the iris. After performing the automatic focusing process, the camera information collecting unit 161 acquires the images of the user's face with the eyes, i.e., irises, and transfers them to the eye tracking determination unit 163. The mobile device 100 stores a list of user functions associated with eye tracking in the storage unit 150 in order to determine whether a user function associated with eye tracking is activated. If a specific user function is activated, the camera information collecting unit 161 identifies it in the list and activates the camera unit 170 to support it via eye tracking.

The eye tracking determination unit 163 analyzes an image transferred from the camera information collecting unit 161 and the gaze angle of the eye therein and transfers the analysis result to the function operating unit 165. To this end, the eye tracking determination unit 163 may use the eye tracking algorithm 153 stored in the storage unit 150. The eye tracking determination unit 163 first performs the face recognition in the received image and extracts the eye portion from the face image. The eye tracking determination unit 163 identifies the gaze angle of the eye from the eye portion. For example, in some embodiments, when the position and orientation of the user's eyes relative to the front surface of the display are such that the user is determined to be gazing at any point on the screen, the gaze angle can be considered zero degrees. In other applications, such as an e-book reader application described in connection with FIG. 5, the gaze angle is analyzed to determine the point on the screen at which the user is currently gazing.

A gaze angle, which can also be considered a gaze "direction," can also be detected via the algorithm as equaling zero degrees when the user's face is determined to be substantially in front of the display, and the gaze direction is detected as parallel to a normal to the front surface of the display. A gaze angle of zero degrees can also be detected via the algorithm if the user's face is substantially centered in an image and the image of the user's irises is substantially centered in the imaged eyes. A zero degree gaze angle can also be detected if the user's head is offset from the front of the display, but the user is directly gazing at the front of the display by viewing it from the corners of her eyes.

A non-zero degree gaze angle could be determined automatically if the user's face is no longer detected, e.g., the user has put down the mobile device or walked away from it.

With the gaze angle determined, the eye tracking determination unit 163 can, in at least some embodiments, determine the point on the display unit 140 where the user gazes (or if the user is no longer gazing), based on the identified gaze angle. In addition, the eye tracking determination unit 163 transfers the identified gaze angle to the function operating unit 165.

The function operating unit 165 determines whether to alter or maintain the state of a currently executed user function based on the information regarding the identified gaze angle transferred from the eye tracking determination unit 163. To this end, the function operating unit 165 identifies a currently executed user function and generates a command according to the gaze angle information. The function operating unit 165 can control a user function according to the generated command. In an embodiment of the invention, the eye tracking function may be applied to the mobile device 100, periodically or in real time. Therefore, the function operating unit 165 may alter or maintain a user function corresponding to a gaze angle that is periodically received. If the function operating unit 165 receives a gaze angle that differs from the previously received value—i.e., a newly detected gaze angle is outside a predetermined range associated with the performance of the currently executed user function, e.g., a range of zero+/−X degrees—it changes the current user function to another user function. If the function operating unit 165 receives the same gaze angle as the previously received value, it maintains the user function.

As described above, the mobile device 100 according to the invention can control, while a specific user function is being executed, the function effectively and adaptively via eye tracking, without operating an additional touch action or an input button. A detailed description of the mobile device 100 for controlling user functions based on eye tracking is described as follows referring to the accompanying drawings.

Figure 3:
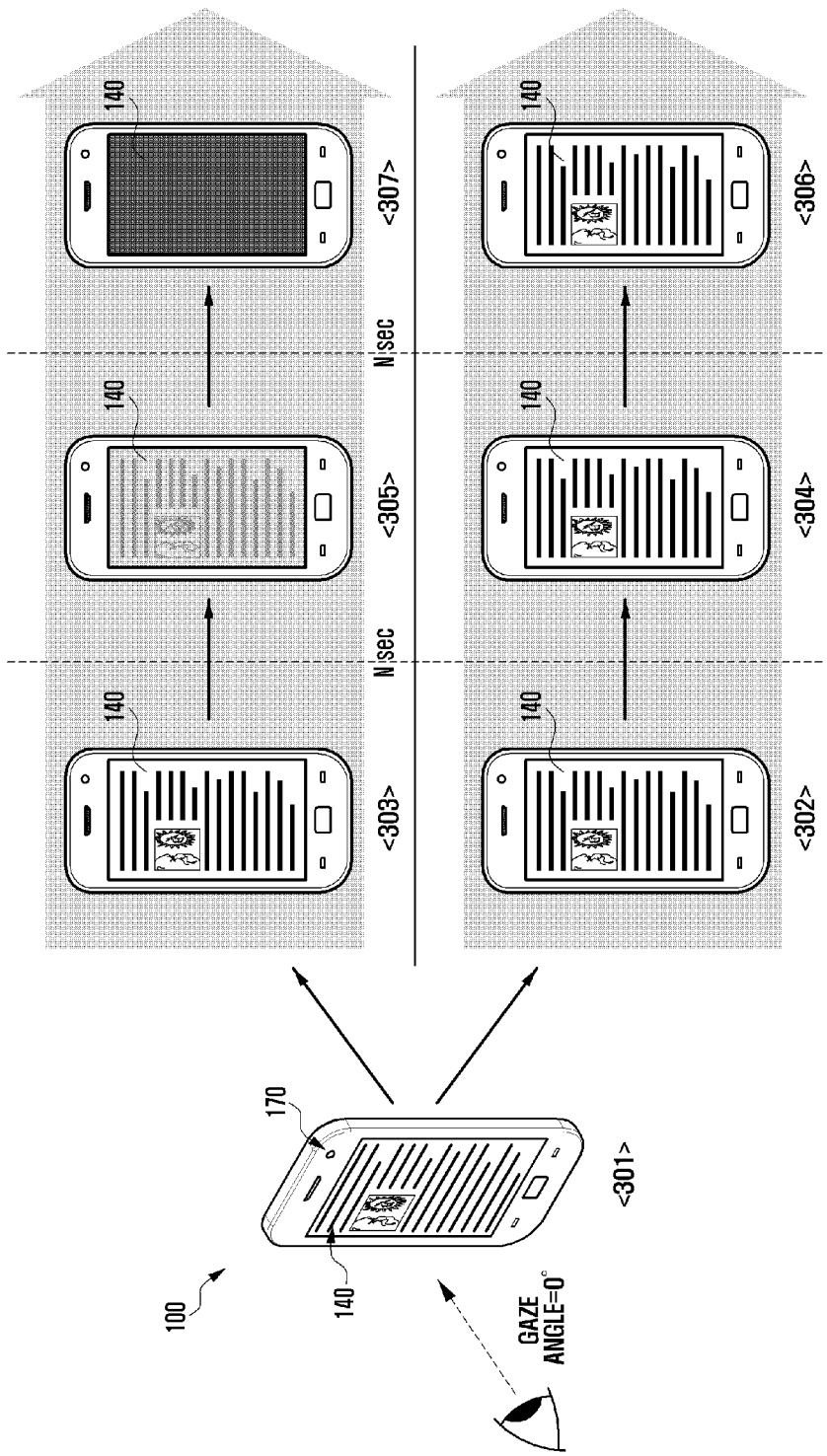
FIG. 3 illustrates user interface screens that support user functions via eye tracking, according to an embodiment of the invention.

FIG. 3 illustrates user interface screens that support user functions via eye tracking, according to an embodiment of the invention. In this embodiment, the mobile device 100 alters the mode where a user function is executed to a power save mode, e.g., a low illumination mode that may be followed by a sleep mode (display turned off), via eye tracking.

Referring to FIG. 3, if the user operates the mobile device 100 to activate a specific user function, e.g., a content view function, it activates an illumination function of the display unit 140. To this end, the mobile device 100 supplies, if the display unit 140 includes a backlight, electric power to the backlight, whereby it emits a certain level of light. Alternatively, if the display unit 140 includes OLEDs, the mobile device 100 supplies electric power to them, controlling emission of a certain level of light. In conjunction with the background illumination, the mobile device 100 retrieves the user's selected content and displays it on the display panel 141 as shown in diagram 301 of FIG. 3.

If the mobile device 100 ascertains that the content view function is associated with eye tracking, it activates the camera unit 170 and recognizes the iris of the user's eye. In diagram 301, a user's iris is illustrated pointing in a direction normal to the front surface of the display, coinciding with a gaze angle of zero degrees as discussed earlier. Thereby, it is ascertained that the user is gazing at the display. Hereafter, a gaze angle of zero degrees (i.e., zero degrees+/−x degrees, where x is predetermined) will be used as an example of a detection that the user is gazing at the display. A non-zero gaze angle will be referred to as a detected angle in which the user is not gazing at the display, or the presence of the user's face is no longer detected. A non-zero gaze angle will also be referred to as a "first gaze angle". If the mobile device 100 ascertains that the user doesn't gaze at the display unit 140 via the acquired gaze angle, it alters the levels of light, step by step, as shown in diagram 303, 305, and 307. That is, if the mobile device 100 identifies a non-zero gaze angle of the user's eye, meaning that the user doesn't gaze at the display unit 140, it controls the display unit 140 to emit a certain level of light for a first period of time as shown in diagram 303. The level of light in diagram 303 may be lower than the level in diagram 301. After that, if the mobile device 100 ascertains that the non-zero gaze angle is maintained for the first period of time, i.e., the user has not gazed at the display unit 140 for the first period of time, it controls the display unit 140 to reduce the amount of emitted light to a lower level than the previous level as shown in diagram 305. After that, if the mobile device 100 ascertains that the non-zero gaze angle is still maintained for a second period of time greater than the first period of time, i.e., the user has not gazed the display unit 140 for the second period of time, it controls the display unit 140 to turn off the illumination function as shown in diagram 307. If the mobile device 100 acquires the non-zero gaze angle for a certain period of time after turning off the illumination function, it may operate automatically in a sleep mode.

On the contrary, if the mobile device 100 identifies a zero degree gaze angle of the user's eye (hereafter, "second gaze angle"), meaning that the user gazes at the display unit 140, at a time point that it displays the screen as shown in diagram 305 or 307, it returns to the operation state where the display unit 140 displays the screen in the original level of light as shown in diagram 303. However, if the mobile device 100 identifies the second gaze angle of the user's eye in a certain period of time from a time point that it entered a sleep mode (as shown in diagram 307), it may display a lock screen for releasing the locked screen, to which the mobile device 100 automatically locks the screen when entering the sleep mode according to a preset routine. To this end, the mobile device 100 needs to activate the camera unit 170 to support eye tracking, for a preset time period, in a state where the display unit 140 is turned off as shown in diagram 307, a state where the mobile device 100 enters a sleep mode, or a state where a certain period of time has elapsed from a time point that the mobile device 100 entered a sleep mode. In addition, the mobile device 100 may also stop eye tracking according to the state where the display unit 140 is turned off as shown in diagram 307, the state where the mobile device 100 enters a sleep mode, or the state where a certain period of time has elapsed from a time point that the mobile device 100 entered a sleep mode. That is, if the display unit 140 is turned off, the mobile device 100 enters a sleep mode, or a certain period of time has elapsed from a time point that the mobile device 100 entered a sleep mode; the mobile device 100 may stop eye tracking and disable the camera unit 170.

Meanwhile, if the user continues to gaze at the display unit 140 while displaying a screen as shown in diagram 301, i.e., the mobile device 100 acquires the second gaze angle, the mobile device 100 controls the display unit 140 to maintain the same state showing the screens as shown in diagrams 302, 304, and 306. The mobile device 100 may not execute a mode where the current state is automatically altered to another state until a certain condition is satisfied or until it receives an input signal in a preset period of time. Therefore, although the user has read the content on the display unit 140 for a relatively long period of time without generating an input signal, the mobile device 100 does not enter a sleep mode or reduce the level of light. This allows the user to conveniently use the mobile device 100 while executing the content view function. By contrast, in conventional devices, a display dimming/sleep mode is automatically entered if no new input command is received within a predetermined time period, even if the user continues to read a current content screen. This annoyance is eliminated with presently described embodiment of FIG. 3.

Figure 4:
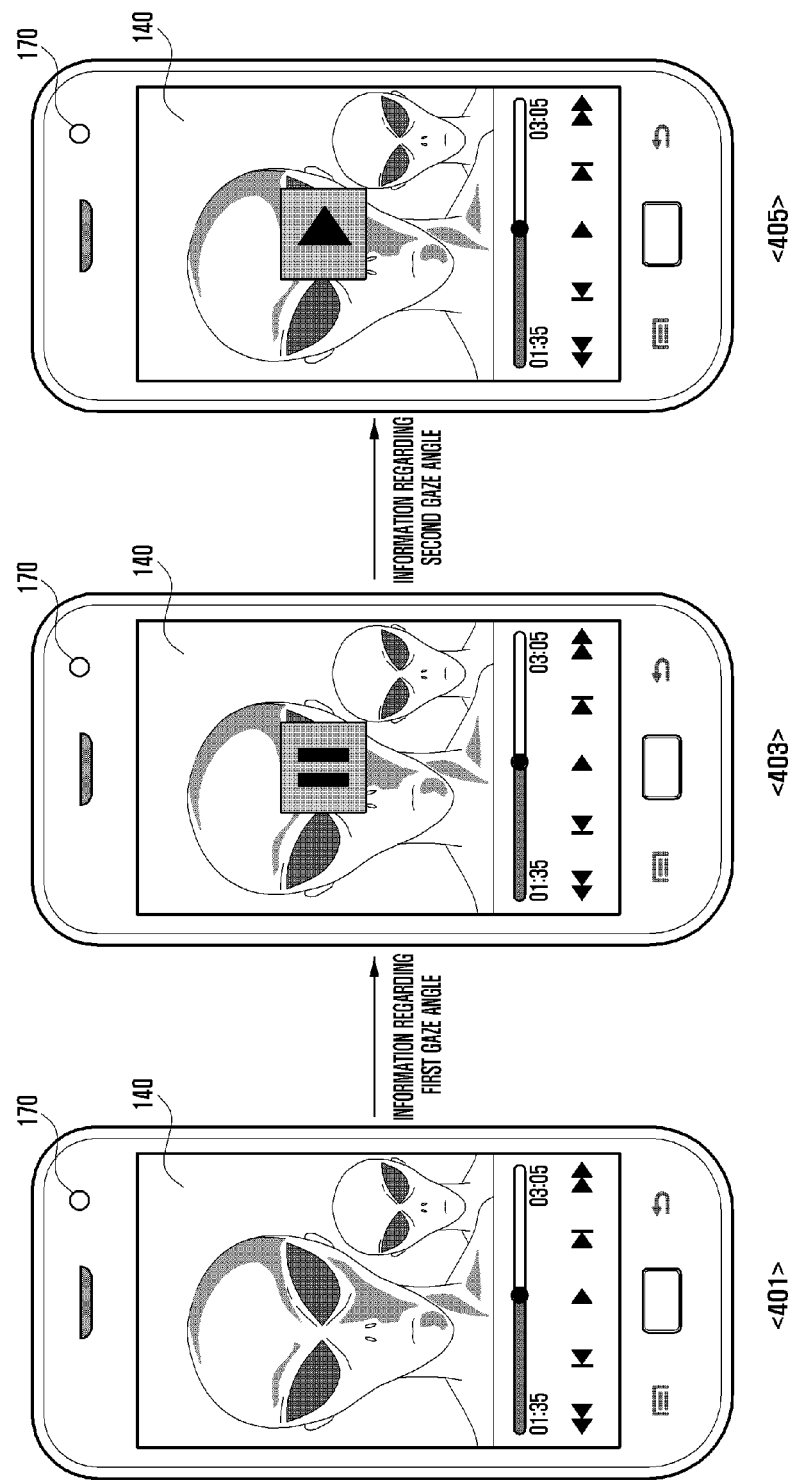
FIG. 4 illustrates user interface screens that support user functions via eye tracking, according to another embodiment of the invention.

FIG. 4 illustrates user interface screens that support user functions via eye tracking, according to another embodiment of the invention. In this embodiment, the mobile device 100 controls the content playback function via eye tracking.

Referring to FIG. 4, the user operates the mobile device 100 to execute a content playback function. To this end, the user selects the corresponding content in the storage unit 150, and operates the mobile device 100 to generate a command for playing it back. For example, if the user requests to play back a video, the mobile device 100 calls an application program for playing it back and controls the display unit 140 to display a screen according to the playback as shown in diagram 401.

The mobile device 100 identifies whether the content playback function is associated with eye tracking. If so, it activates the camera unit 170 and acquires images periodically or in real time, in order to support the eye tracking function (which is assumed for diagram 401).

If the mobile device 100 acquires the first (non-zero) gaze angle of the user's eye, meaning that the user does not gaze at the display unit 140, while executing the eye tracking function, it enters a mode where it displays a screen as shown in diagram 403 and pauses the content playback. For instance, if the mobile device 100 acquires the first gaze angle of the user's eye immediately since the user does not gaze at the display unit 140, it enters a mode where it pauses the content playback, as shown in diagram 403. To this end, the mobile device 100 executes the eye tracking function in real time. Alternatively, the pause operation is implemented only if the mobile device 100 acquires the first gaze angle for more than a predetermined minimum period of time.

If the user gazes the display unit 140 in a state where it displays the screen as shown in diagram 403, i.e., if the mobile device 100 acquires the second (zero degree) gaze angle while the eye tracking function is executed, the mobile device 100 releases the mode where it has paused the content playback and resumes playing back the content as shown in diagram 405. Therefore, the mobile device 100 according to this embodiment pauses, if the user does not gaze at the display unit 140 playing back the content, the content playback without an additional operation, and then resumes playing it back if the user gazes at the display unit 140 again.

If the mobile device 100 continues to acquire the non-zero gaze angle for a certain period of time, when it displays the screen as shown in diagram 403, it turns off the display unit 140. Alternatively, the mobile device 100 may turn off the display unit 140 and also terminate the content playback function. As another alternative, the mobile device 100 terminates the content playback function after a certain period of time has elapsed from a time point that it turns off the display unit 140. In addition, the mobile device 100 may terminate the eye tracking function at a time point when the display unit 140 is turned off or when the content playback function is terminated, thereby preventing electric power consumption according to the activation of the camera unit 170. After that, if the mobile device 100 acquires the second gaze angle via eye tracking, it enters a playback mode such as that shown in diagram 405.

Figure 5:
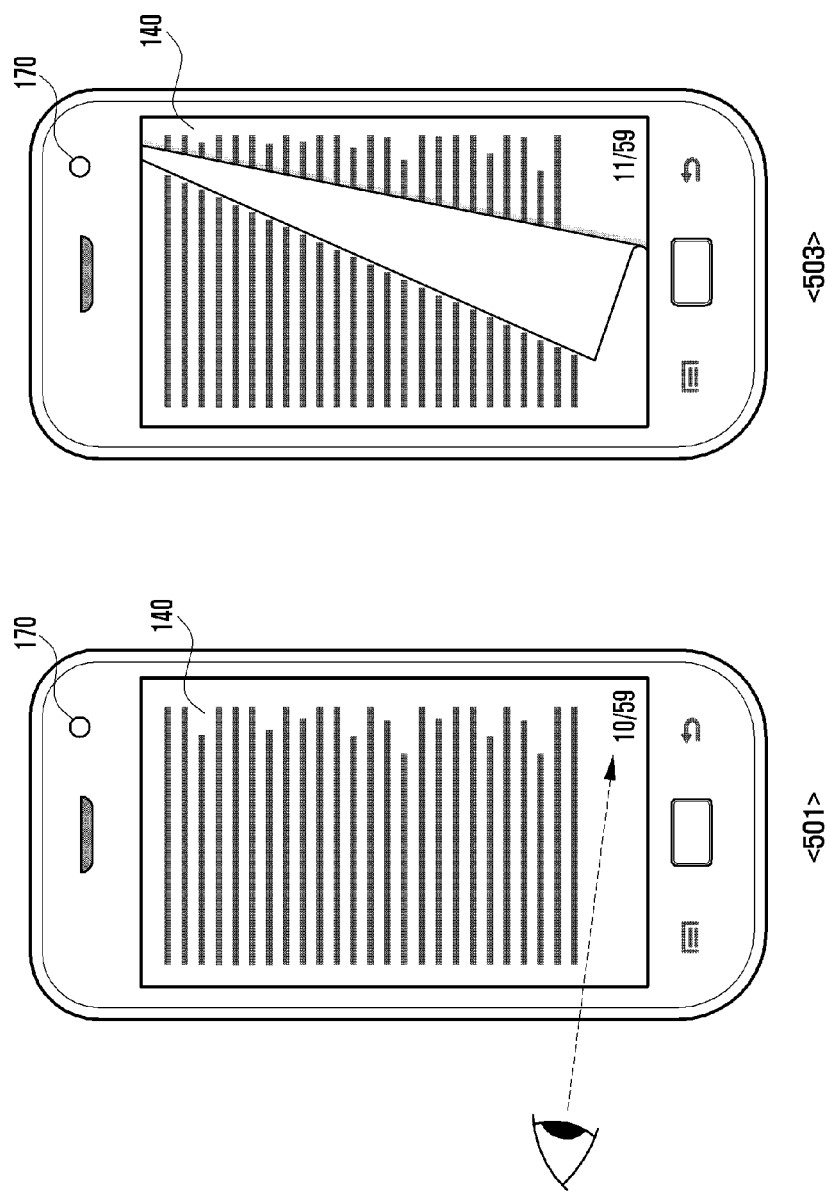
FIG. 5 illustrates user interface screens that support user functions via eye tracking, according to a further embodiment of the invention.

FIG. 5 illustrates user interface screens that support user functions via eye tracking, according to a further embodiment of the invention. In the embodiment, the mobile device 100 controls an e-book content view function via eye tracking.

Referring to FIG. 5, the user selects an e-book content view function in the mobile device 100. To this end, the mobile device 100 stores the e-book content in the storage unit 150 and also an application for playing back it. If the user generates signals for selecting the corresponding e-book content and playing it back, the mobile device 100 plays it back on the screen as shown in diagram 501. In addition, the mobile device 100 determines whether the e-book content view function is associated with eye tracking. If it is associated with eye tracking, a determination of whether the eye tracking mode is activated is made. If eye tracking is activated, the camera unit 170 acquires images periodically or in real time via eye tracking.

If the mobile device 100 tracks the user's eye positions and identifies that the user views the display unit 140 at a preset gaze angle, it turns over the page as shown in diagram 503. For example, if the mobile device 100 acquires a gaze angle at which the user is looking at the bottom right corner portion on the display unit 140, it detects this gaze angle detection as a command for turning the page to the next page. If the mobile device 100 continues to acquire this gaze angle for a certain period of time, it detects it as a command to continue turning pages.

Therefore, the mobile device 100 allows the user to conveniently turn pages of the e-book, via eye tracking, without an additional command corresponding to a touch action or an input signal. In some implementations, mobile device 100 may adaptively alter the application period of eye tracking. That is, the mobile device 100 checks and stores the number of pages turned over, and activates the camera unit 170 in order to support eye tracking, for a certain period of time, before an estimated time point that an event for turning over pages will occur, according to the information. For example, if it takes an average of two minutes for the user to turn to the next page, the mobile device 100 disables the camera unit 170 for a "camera disabling time" shorter than the average page turning interval. For instance, after an event for turning a page occurred, the camera is disabled and then enabled again after 1 minute 30 seconds or 1 minute 40 seconds has elapsed from the time point that the event occurred in order to support eye tracking. If the page turning interval has gradually shortened, the mobile device 100 may dynamically reduce the camera disabling time corresponding to the shortened interval, so that it can support the eye tracking function. To this end, the mobile device 100 may estimate the average page turning interval via a preset number of pages. For example, the mobile device 100 may limit the number of pages turned over to three, estimate the average page turning interval with respect to the three turned pages, and then define the camera disabling time to support the eye tracking function. This method prevents the camera unit 170 from wasting electric power, compared with a state where the camera unit 170 remains enabled despite not executing the eye tracking function.

If the mobile device 100 displays the last page of the e-book content on the display unit 140, it may automatically terminate the eye tracking function.

Meanwhile, if the mobile device 100 acquires a user's gaze angle for selecting the previous page, e.g., a gaze angle at which the user gazes at the bottom left corner portion on a page, it detects it as a command for turning the page to the previous page and then performs the page turning operation to the previous page. In addition, the mobile device 100 may also define the page turning speed according to the period of time for which it acquires a gaze angle at which the user gazes at the bottom right or left portion on a page. That is, if a user gazes at the bottom right or left portion on a page for a certain period of time, the mobile device 100 may set the page turning speed so that it gradually increases or is maintained over a preset value. Therefore, the user can rapidly search for a corresponding page. As described above, the mobile device 100 can control the page turning speed according to the period of time for which it acquires a gaze angle for turning pages, and stop turning pages if it acquires a gaze angle that differs from the gaze angle for turning pages. The embodiment of FIG. 5 is particularly advantageous for helping a disabled or paralyzed person read an e-book.

Figure 6:
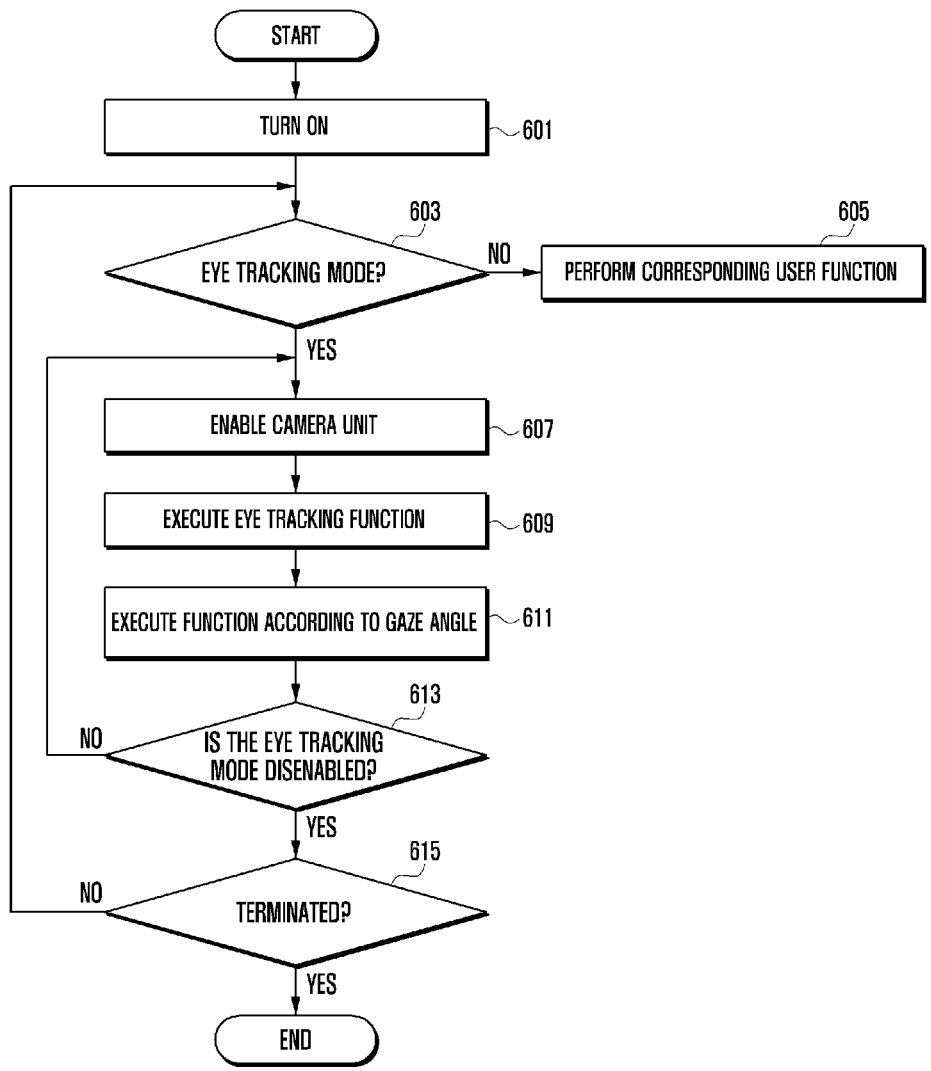
FIG. 6 illustrates a flow chart that describes a method for controlling a user function based on eye tracking, according to an embodiment of the invention.

FIG. 6 is a flow chart that describes a method for controlling a user function based on eye tracking, according to an embodiment of the invention. At the start, the controller 160 (hereafter, "the controller" for brevity) supplies electric power to the components in the mobile device 100 (601). At this point, the controller is ready to execute user functions via eye tracking.

If the user generates a signal to execute a specific user function, the mobile device 100 executes it. During this process, the controller determines whether an eye tracking mode is set (603). For example, the controller identifies whether the user function is associated with eye tracking, and, if the user function is associated with eye tracking, whether the eye tracking mode is activated. If the eye tracking mode is not set at step 603, the activated user function is controlled according to the input signal (605).

On the contrary, if the eye tracking mode is set at step 603, the camera unit 170 is activated (607). The controller controls the camera unit 170 to acquire images. After acquiring the images, the controller executes the eye tracking function (609). That is, the positions of the user's eyes are identified as well as the gaze angle according to the eye positions.

The controller performs a corresponding operation according to the gaze angle (611). For example, if the controller ascertains that the user gazes at the display unit 140 (hereafter, "the display"), according to the acquired gaze angle, in a state where a content view function or a content playback function has been executed, it maintains the execution of the content view function or the content playback function. That is, the controller supplies electric power to the display and controls the display to display the content. On the contrary, if the controller ascertains that the user doesn't gaze at the display based on the acquired gaze angle, it controls the display to reduce the level of brightness or turns off the display, or pauses or terminates the content playback. If an e-book playback function has been executed, the controller controls the page turning operation of the e-book according to the acquired gaze angles.

If the controller acquires a gaze angle at which the user gazes at the display during the reception of a call connection request message, it performs an automatic call connection. This is described in detail referring to FIG. 7. As shown in FIG. 7, if the mobile device 100 receives a call connection request message from another mobile device, the controller is awakened from the sleep mode or displays a screen informing that a call connection request message is received in an idle state, as shown in diagram 701. The controller ascertains that the call connection function is associated with eye tracking and activates the camera unit 170. The controller activates the camera unit 170 for a certain period of time and identifies whether to identify a preset gaze angle from the acquired image. If the controller identifies a preset gaze angle from the acquired image, it performs an automatic call connection as shown in diagram 703.

If the call connection request is ended while maintaining the execution of the eye tracking function, the controller may terminate the eye tracking function. The controller may execute the eye tracking function for only a preset period of time, so that a corresponding function is terminated when the preset period of time has elapsed. If a call is connected and then the call function terminated, the controller may terminate the eye tracking function. If a call is connected via eye tracking and the controller acquires a gaze angle at which the user gazes at the display after a certain period of time has elapsed from a time point that the call connection was established, the controller may terminate the call connection. In addition, the controller may also establish a call connection by matching information, acquired via a face recognition procedure, as well as a gaze angle of the user's eyes, with the user's preset information. For example, only if the controller identifies a face that was registered, as a mobile device owner's face, in the mobile device, it can acquire the gaze angle and establish a call connection according to the acquired gaze angle.

After performing a corresponding operation according to the gaze angle at step 611, the controller determines whether an event for releasing the eye tracking mode occurs (613). If so, the controller determines whether a signal for terminating the procedure is input (615). Examples of an event for releasing the eye tracking mode may be a case where the controller acquires a gaze angle at which the user doesn't gaze at the display for a certain period of time or a case where a touch action or an input signal for releasing the eye tracking mode is generated.

On the contrary, if the controller ascertains that an event for releasing the eye tracking mode has not occurred at step 613, it returns to and proceeds with step 607. In addition, if the controller ascertains that a signal for terminating the procedure is not input at step 615, it returns to and proceeds with step 603.

Although the embodiment just described includes a step for determining whether the eye tracking mode is activated, as an alternative, the eye tracking mode can be executed by default.

As described above, methods according to the invention can control user functions in a mobile device, such as altering the states or maintaining the current state, via eye tracking, without requiring additional operations such as the application of touch actions or the generation of input signals, thereby facilitating use of the mobile device. In particular, if the invention is applied to mobile devices with large displays and typically held in one hand and operated by the other, use thereof is facilitated via eye tracking.

As described above, the method and the mobile device adapted thereto, according to the invention, can control efficiently and adaptively a variety of functions, based on eye tracking, so that users can conveniently use the mobile device.

Although not shown in the drawings, the mobile device may selectively further include various types of components, for example: a short-range communication module for short-range communication; an interface for transmitting/receiving data in a wireless or wired mode; an Internet communication module; and a digital broadcast module for receiving and reproducing broadcasts. With the spread of digital convergence, although it is unnecessary to list all the modifications of mobile devices in this description, it will be easily appreciated to those skilled in the art that the other components equivalent to the above-listed components may be further included to the mobile device according to the invention. Also, it will be appreciated that, according to specific applications, the mobile device may be implemented by omitting a particular component or replacing it with other components.

The above-described methods implemented via controller 160 according to the present invention can be implemented in hardware, firmware or as software or computer code that can be stored in a recording medium such as a CD ROM, an RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

The terms or words described in the present description and the claims should not be limited by a general or lexical meaning, instead should be analyzed as a meaning and a concept through which the inventor defines and describes the exemplary embodiments of the invention at his best effort. Therefore, one skilled in the art will understand that the embodiments disclosed in the description and configurations illustrated in the drawings are only exemplary embodiments, instead there may be various modifications, alterations, and equivalents thereof to replace the embodiments at the time of filing this application. Although exemplary embodiments of the invention have been described in detail hereinabove, it should be understood that many variations and modifications of the basic inventive concept herein described, which may be apparent to those skilled in the art, will still fall within the spirit and scope of the exemplary embodiments of the invention as defined in the appended claims.

What is claimed is:

1. A method for operating user functions in a mobile device having a display, comprising:
   executing a specific user function;
   acquiring an image via a camera unit of the mobile device while the specific user function is executed;
   acquiring a gaze angle of a user's eye from the acquired image and determining from the acquired image whether the user gazes at the display; and
   executing an eye tracking function in which execution state of the user function is controlled according to the gaze angle, wherein a page turning interval speed is controlled according to a time period for which a gaze angle at which the user gazes at the same point on the display is acquired.

2. The method of claim 1, further comprising:
   prior to activating the camera unit, determining whether the specific user function is associated with eye tracking, and if so, whether an eye tracking mode is activated.

3. The method of claim 1, wherein the execution of an eye tracking function further comprises at least one of the following:
   reducing a level of illumination of the display when the acquired gaze angle is a first gaze angle indicating that the user doesn't gaze at the display;
   turning off the display;
   terminating the user function execution;
   pausing the user function execution; and
   setting or unlocking a touch lock of a touch panel of the display.

4. The method of claim 3, wherein the execution of an eye tracking function further comprises at least one of the following:
   if the acquired gaze angle is a second gaze angle indicating that the user gazes at the display, restoring an illumination level of the display to an original level of illumination;
   turning on the display;
   re-executing the user function;
   resuming the user function execution that is paused; and
   unlocking or setting a touch lock of the touch panel that is locked.

5. The method of claim 1, further comprising, when the specific user function is a content playback function, pausing or terminating execution of the user function comprises pausing content playback when determining that the user does not gaze at the display over a preset period of time, and, following the pausing, resuming content playback when determining that the user again gazes at the display.

6. The method of claim 1, wherein the execution of an eye tracking function comprises:
   maintaining a current screen of the display when the acquired gaze angle is a second gaze angle indicating that the user gazes at the display.

7. The method of claim 1, wherein the acquisition of a gaze angle comprises:
   detecting presence of a face of a subject;
   automatically focusing on an iris in the detected face; and
   acquiring a gaze of the automatically focused iris of the subject.

8. The method of claim 1, wherein the execution of an eye tracking function comprises:
   when the acquired gaze angle is a second gaze angle indicating that the user gazes at the display in a state where a call connection request message is received, automatically establishing the call connection.

9. The method of claim 1, further comprising pausing or terminating execution of the user function when determining that the user does not gaze at the display over a preset period of time.

10. A method for operating user functions in a mobile device, comprising:
    executing an e-book function;
    acquiring an image via a camera unit of the mobile device while the e-book function is executed;
    acquiring a gaze angle of a user's eye from the acquired image;
    turning a page of e-book content when the acquired gaze angle is a gaze angle at which the user gazes at a certain point in a display unit of the mobile device where the e-book content is displayed;
    determining an average page turning interval; and
    periodically disabling the camera unit for a camera disabling time shorter than, and determined in relation to, the average page turning interval.

11. A mobile device comprising:
    a camera unit that acquires images of a subject;
    a controller configured to acquire a gaze angle of a user's eye from an image acquired via the camera unit, and to execute an eye tracking function in which an execution state of a user function is controlled according to the gaze angle; and a storage unit that stores data corresponding to the user function, and a program to track gaze angles of a user's eye;

wherein the controller automatically establishes a call connection, if the acquired gaze angle is an angle indicating that the user gazes at a display unit of the mobile device in a state where a call connection request message is received.

12. The mobile device of claim 11, wherein the storage unit stores a list of user functions associated with eye tracking.

13. The mobile device of claim 11, wherein if the acquired gaze angle is an angle indicating that the user doesn't gaze at the display unit, an illumination level of the display unit is reduced or the display unit is turned off.

14. The mobile device of claim 13, wherein the controller disables the camera unit if the display unit is turned off or the user function execution is terminated.

15. The mobile device of claim 11, wherein, if the controller acquires a first gaze angle indicating that the user doesn't gaze at the display unit over a preset period of time, it pauses or terminates the user function execution.

16. The mobile device of claim 11, wherein the controller: sets or unlocks a touch lock of a touch panel of the display unit if the acquired gaze angle is a first gaze angle indicating that the user doesn't gaze at the display unit; and unlocks or sets a touch lock of a touch panel of the display unit if the acquired gaze angle is a second gaze angle indicating that the user gazes at the display unit.

17. The mobile device of claim 11, wherein the camera unit automatically focuses on the iris of the user's eye during the acquisition of images of a subject.

18. A mobile device comprising:
a camera unit that acquires images of a subject;
a controller configured to acquire a gaze angle of a user's eye from an image acquired via the camera unit, and to execute an eye tracking function in which an execution state of a user function is controlled according to the gaze angle; and
a storage unit that stores data corresponding to the user function, and a program to track gaze angles of a user's eye;
wherein the controller is configured to determine an average page turning interval of e-book content, and periodically disable the camera unit for a camera disabling time shorter than, and determined in relation to, the average page turning interval.

19. The mobile device of claim 18, wherein the controller turns a page of e-book content when the acquired gaze angle is a gaze angle at which the user gazes at a certain point in a display unit of the mobile device where the e-book content is displayed.

20. The mobile device of claim 19, wherein the controller controls a page turning interval speed according to a time period at which a gaze angle at which the user gazes at the same point in the display unit is acquired.

* * * * *